(12) United States Patent
Villa et al.

(10) Patent No.: US 6,271,375 B1
(45) Date of Patent: Aug. 7, 2001

(54) ORTHO-METALATION PROCESS FOR THE SYNTHESIS OF 2-SUBSTITUTED-1-(TETRAZOL-5-YL)BENZENES

(75) Inventors: Marco Villa, Milan; Pietro Allegrini, Lonigo; Katiuscia Arrighi, Cabiate; Maurizio Paiocchi, Milan, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/445,470
(22) PCT Filed: Jun. 29, 1998
(86) PCT No.: PCT/EP98/03969
§ 371 Date: Apr. 27, 2000
§ 102(e) Date: Apr. 27, 2000
(87) PCT Pub. No.: WO99/01459
PCT Pub. Date: Jan. 14, 1999

(30) Foreign Application Priority Data

Jun. 30, 1997 (IT) .............................. MI97A1544

(51) Int. Cl.⁷ .................................. C07D 471/00
(52) U.S. Cl. .................... 544/279; 548/250; 548/252; 548/253
(58) Field of Search .................... 548/250, 252, 548/253; 544/279

(56) References Cited

U.S. PATENT DOCUMENTS

| | | | |
|---|---|---|---|
| 5,039,814 | 8/1991 | Shuman et al. | 548/250 |
| 5,149,699 | 9/1992 | Ellingboe et al. | 514/258 |
| 5,256,654 | 10/1993 | Ellingboe et al. | 514/186 |
| 5,278,312 | 1/1994 | Chekroun et al. | 548/110 |
| 5,310,929 | 5/1994 | Ardecky et al. | 548/253 |
| 5,371,233 | 12/1994 | Daumas et al. | 548/250 |
| 5,382,672 | 1/1995 | Chekroun et al. | 548/110 |
| 5,498,776 | 3/1996 | Ellingboe et al. | 514/183 |
| 5,760,220 | 6/1998 | Giguere et al. | 540/521 |
| 5,977,372 | * 11/1999 | Giguere et al. | 548/103 |

\* cited by examiner

*Primary Examiner*—Fiona T. Powers
(74) *Attorney, Agent, or Firm*—Arent Fox Kintner Plotkin & Kahn PLLC

(57) ABSTRACT

A process of direct metalation of phenyltetrazoles useful for preparing compounds of formula (II) intermediates for the synthesis of angiotensin II antagonists is described.

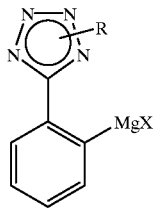

(II)

11 Claims, No Drawings

ORTHO-METALATION PROCESS FOR THE SYNTHESIS OF 2-SUBSTITUTED-1-(TETRAZOL-5-YL)BENZENES

The present invention relates to a process useful for the synthesis of 2-substituted-1-(tetrazol-5-yl)benzenes and, more particularly, it relates to a process of direct ortho-metalation of (tetrazol-5-yl)benzene useful for the preparation of 2-substituted-1-(tetrazol-5-yl)benzenes, well-known intermediates for angiotensin II antagonists. The angiotensin II antagonists constitute a new therapeutic class, whose parent compound losartan (INN) has been recently launched on the pharmaceutical market as drub useful for the treatment of hypertension, anxiety, glaucoma, heart attack. Most of the compounds belonging to the class of angiotensin II antagonists has a common biphenyltetrazolyl moiety.

Compounds such as the already mentioned losartan, candesartan, irbesartan, tasosartan and valsartan, to list the most known compounds of this therapeutic class, are all represented by the following general formula

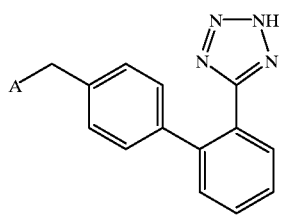

(I)

in which A is an optionally substituted nitrogen containing heterocycle or an open amide residue In particular the A residue has the following meanings, for the different previously identified angiotensin II antagonists:

losartan-A=2-butyl-4-chloro-5-hydroxymethyl-imidazol-1-yl candesartan-A=2-ethoxy-7-carboxy-1H-benzimidazol-1-yl irbesartan-A=2-butyl-1,3-diaza-spiro[4.4]non-1-en-4-on-3-yl tasosartan-A=2,4-dimethyl -5,8-dihydro-6H-pyrido[2,3-d]pyrimidin-7-on-8-yl valsartan-A=(S)-N-(1-carboxy-2-methylprop-1-yl)-N-pentanoylamino It is evident that one of the key intermediates useful in the synthesis of the compounds of formula I is represented by 2-substituted phenyltetrazole derivatives of formula

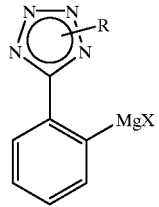

(II)

in which R is a hydrogen atom, a protective group or a salifying group and X is a halogen atom selected among chlorine, bromine and iodine.

The intermediates of formula II are used in a cross-coupling reaction with a suitable substituted phenyl derivative to obtain the biphenyl portion of the compounds of formula I.

In our knowledge, among the literature methods for the preparation of the compounds of formula II, only one method that involves a direct metalation, that is an exchange reaction between a hydrogen atom and a metal, is reported. In particular this method is described in the U.S. Pat. No. 5,039,814 (Merck & Co. Inc.) and, in effect, it involves the ortho-lithiation of phenyltetrazole followed by a transmetalation reaction.

A disadvantage of this process is represented by the necessity to use organolithium compounds that require particular safety procedures to be used on a large scale, because of their high inflammability and reactivity.

The most common alternative to the direct metalation of phenyltetrazoles is the metalation of the corresponding 2-halo-substituted derivative, that is an exchange reaction between a halogen atom and a metal, as described, for example, in the European patent applications No. 550313 (Synthelabo) and No. 539086 (American Home Products Corp.).

It would be advantageous to prepare the phenyltetrazoles of formula II by direct metalation, avoiding the use of compounds that require particular safety procedures such as organolithium compounds.

Some methods for the direct metalation of activated organic compounds that do not involve lithium derivatives are well-known from the literature. Von Adrian Marxer et al. in Helvetica Chimica Acta, 57(7), 1988–2000 (1974) describe the use of ethylmagnesium bromide for the direct ortho-metalation of phenylpyrazoles with very good results.

Philip E. Eaton et al. in J. Am. Chem. Soc., 111(20), 8016–8018 (1989) reported the direct ortho-metalation of cubanes and of aromatic substrates by using an excess of a Hauser base, that is of a compound of formula $R_2NMgBr$. Nevertheless our attempts to carry out the direct ortho-metalation of a phenyltetrazole to obtain a compound of formula II, following the methods described in the literature, were quite disappointing. In particular, using ethylmagnesium bromide no ortho-metalated product was formed whereas using a strong excess of a Hauser base the conversion was so low to make the process not practicable. Now we have found that the compounds of formula II can be prepared by direct ortho-metalation of the corresponding phenyltetrazole without using organolithium compounds.

Therefore, object of the present invention is a process of direct ortho-metalation for the preparation of compounds of formula

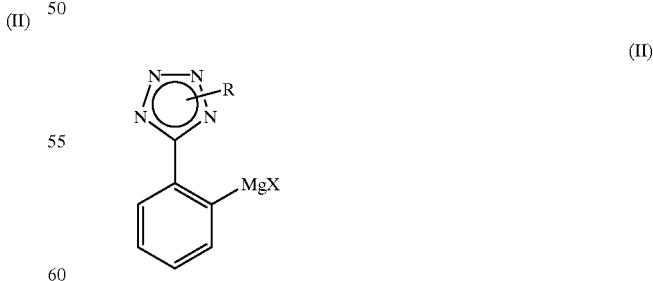

(II)

in which

R is a hydrogen atom, a protective group or a salifying group and X is a halogen atom selected among chlorine, bromine and iodine, that involves the treatment of a compound of formula

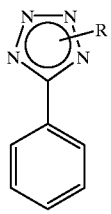

(III)

in which R has the above reported meanings, with a Grignard compound of formula $$R_1\text{-MgX} \qquad (IV)$$

in which X has the above reported meanings and $R_1$ is a straight or branched $C_1$–$C_6$ alkyl group or a benzyl group; in the presence of a catalytic amount of a secondary amine of formula $$R_2\text{-NH-}R_3 \qquad (V)$$

in which $R_2$ and $R_3$, the same or different, are branched or cyclic $C_3$–$C_6$ alkyl groups or trialkylsilyl groups having from 1 to 3 carbon atoms in the alkyl moiety or $R_2$ and $R_3$ together with the NH group form an optionally substituted cyclic amine. The process object of the present invention is useful for the preparation of intermediates for the synthesis of angiotensin II antagonists.

The protective groups of the tetrazole moiety are those commonly used in the known syntheses of angiotensin II antagonists and they mainly consist of straight or branched $C_1$–$C_6$ alkyl groups, optionally mono or poly substituted with aryl groups such as phenyl or pyridyl or with arylalkoxy groups, and of $C_1$–$C_3$ alkoxy or alkylthio groups.

In the process object of the present invention the preferred protective group is tertbutyl.

Sodium and potassium ions are preferably used as salifying groups. The alkyimagnesium halides of formula IV are well-known compounds. Generally they are prepared from the corresponding alkyl halides by treatment with magnesium.

Preferably an ethylmagnesium halide prepared in situ, more preferably ethylmagnesium bromide, is used.

Generally the amount of the Grignard compound of formula IV is at least stoichiometric, preferably in slight excess compared to the phenyltetrazole of formula II, but amounts even lower then the stoichiometric one are successfully used.

Therefore the molar ratio compound IV: compound III is generally between 1:1 and 1.5:1 more preferably between 1.05:1 and 1.3:1.

The secondary amine of formula V usually has very bulky substituents linked to the NH group.

The amines of formula V are preferably those in which $R_2$ and $R_3$ are branched or cyclic $C_3$–$C_6$ alkyl groups or $R_2$ and $R_3$ together with the NH group form an optionally substituted cyclic amine.

Specific examples of amines having branched or cyclic $C_3$–$C_6$ alkyl groups as $R_2$ and $R_3$ substituents are diisopropylamine, di-tert-butylamine, di-sec-butylamine, tert-butyl-iso-propylamine, di-cyclopentylamine and di-cyclohexylamine.

Preferred examples of amines of formula V wherein $R_2$ and $R_3$ together with the NH group form an optionally substituted cyclic amine comprises pyrrolidines, piperidines and morpholines, which are tetra-substituted at the two vicinal positions to the nitrogen, such as 2,2,6,6-tetramethylpiperidine and 2,2,5,5-tetramethylpyrrolidine. In particular the piperidine derivatives, in turn, can be further substituted at the 4 position by alkyl and alkoxy groups or by an oxo group protected as acetal. Particularly preferred amines of formula V are 2,2,6,6-tetramethylpiperidine and diisopropylamine.

The amines of formula V are used in catalytic amount compared to the Grignard compound IV, that is in a molar amount smaller than the stoichiometric one. Generally the molar ratio compound V: compound IV is between 0.01:1 and 0.5:1, more preferably between 0.05:1 and 0.2:1.

The direct ortho-metalation, object of the present invention, is carried out in a suitable solvent, usually ethers and their mixtures with aliphatic or aromatic hydrocarbons. Preferably tetrahydrofuran, optionally in admixture with toluene, is used as solvent. The temperature is not a critical parameter and, generally, it is between room and reflux temperature.

Preferably it is carried out at the reflux temperature.

Optionally the direct metalation reaction can be carried out by adding catalytic amount of metal salts too, with or without ligands. The compounds of formula II, prepared according to the process object of the present invention, can be directly used in a cross-coupling reaction for the preparation of the biphenyltetrazolyl moiety of the compounds of formula I according to what previously reported.

Alternatively they can undergo a transmetalation reaction according to known techniques to obtain a compound of formula

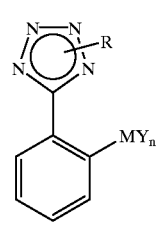

(VI)

in which R has the previously reported meanings, Y has the just reported meanings of X or is an OH, $C_1$–$C_4$ alkoxy or $C_1$–$C_4$ alkyl group, M is selected among Zn, B, Al, Cu and Sn and n is 1, 2 or 3 depending on the meaning of M.

Preferably the compounds of formula II obtained according to the process of the present invention are transmetalated to obtain the compounds of formula VI in which M is Zn and Y is chlorine, bromine or iodine.

The transmetalation is carried out by treating the Grignard compound with a zinc halide, generally $ZnCl_2$.

The transmetalation reaction can be directly carried out by treating the reaction mixture, containing the Grignard compound II, with the suitable zinc halide. The compound of formula VI is used for cross-coupling reactions as reported for the compounds II.

As previously reported the compounds of formula II, prepared according to the process object of the present invention, are useful as intermediates for the preparation of angiotensin II antagonists. In the present context the usefulness of the compounds of formula II is particularly exemplified in the preparation of the compound known as tasosartan according to the cross-coupling process described in the International patent application No. WO 96/40684 (American Home Products Corporation).

A preferred practical embodiment of the process of the present invention is the following:

Ethyl halide was added to a magnesium suspension in a suitable solvent to form the corresponding Grignard compound. After addition of a catalytic amount of 2,2,6,6-tetramethylpiperidine, the mixture was warmed and phenyl-tert-butyltetrazole was added.

At the end of the metalation reaction, that is when the evolution of ethane stopped, the resultant compound of formula II was directly treated with a zinc halide to obtain the corresponding compound of formula VI in which M=Zn, that was used for the cross-coupling reaction, without any isolation or purification.

In our knowledge the metalation process object of the present invention is the only method of direct metalation of phenyltetrazoles that does not use organolithium compounds.

Moreover the use of alkylmagnesium halides together with catalytic amount of a suitably bulky secondary amine is a method of direct metalation of aromatic compounds that, in our knowledge, has never been described in literature. Actually, the prior art describes direct metalation reactions of compounds different from phenyltetrazoles or by simple reaction with ethylmagnesium bromide without any catalyst (see the above mentioned work of Von Adrian Marxer et al.) or by using an excess of Hauser bases (see the above mentioned work of Philip E. Eaton et al.). Nevertheless no method known from the literature is suitable for the direct metalation of phenyltetrazoles (see comparison examples).

It appears evident to the man skilled in the art that the process of direct metalation object of the present invention is an expedient alternative to the lithiation process described in the literature.

Apart from the remarkable advantage of avoiding the use of alkyllithium, the process object of the present invention is particularly advantageous in its practical and industrial realisation because it does not use low temperatures and the obtained crude compounds of formula II can be used either directly in the subsequent cross-coupling reaction or in the transmetalation reaction without any isolation or purification. With the aim to better illustrate the present invention, the following examples are now given:

EXAMPLE 1

Ethylbromide (5.5 g; 50 mmol) was dropped into a stirred suspension of magnesium turnings (1.2 g; 50 mmol) in tetrahydrofuran (25 ml), at 25° C. under inert atmosphere, keeping the temperature below 60° C. At the end of the addition, the mixture was further stirred for 30 minutes at 60° C.; then 2,2,6,6-tetramethylpiperidine (0.72 g, 5 mmol) was added and it was refluxed (73° C.) for 1 hour. Phenyl-tert-butyltetrazole (8.1 g; 40 mmol) was added and the mixture was refluxed, under stirring, for 18 hours (altogether about 1000 ml of gas were evolved). Analysing a sample, after quenching with $CH_3OD$ for $^1H$-NMR, the residual phenyl-tert-butyltetrazole was <5% of the starting amount.

The red-orange solution of tert-butylphenvltetrazolvlmagnesium bromide (40 theoretical mmol) was cooled at 70° C. and was added (the possible residual magnesium can be eliminated by settling) to a suspension of anhydrous zinc chloride (10.4 g; 76.2 mmol) in toluene (30 ml) during 15 minutes. The suspension was warmed at 60° C. for 1 hour. 8-[(4-Bromophenyl)methyl]-5,8-dihydro-2,4 -dimethyl-pyrido[2,3-d]pyrimidin-7(6H)-one (10.4 g; 30 mmol), palladium acetate (0.1 g, 0.44 mmol) and triphenylphosphine (0.35 g; 1.33 mmol) were added and the mixture was kept at 60° C. for 24 hours. The suspension was cooled at 25° C.; water (15 ml) and acetic acid (0.9 g) were added. The two phases were separated and the organic one was washed with water (10 ml) and evaporated to dryness under vacuum.

The residue, analysed by HPLC analysis, contains:

coupling product: 9.48 g (20.3 mmol)

starting material: 1.24 g (3.6 mmol)

EXAMPLE 2

Ethylbromide (2.2 g; 20 mmol) was added dropwise to a stirred suspension of magnesium turnings (0.48 g; 20 mmol) in tetrahydrofuran (10 ml), at 25° C. under inert atmosphere, keeping the temperature below 60° C. At the end of the addition, the mixture was stirred for 30 minutes; then 2,2,6,6-tetramethylpiperidine (0.29 g; 2 mmol) was added and it was refluxed (73° C.) for 1 hour. At the temperature of 65° C., phenyltetrazole sodium salt (2.7 g; 16 mmol). in tetrahydrofuran (10 ml), was added in about 15 minutes. The mixture was kept under stirring, at 65° C., for 18 hours. It was cooled at 60° C., anhydrous zinc chloride (4.15 g; 30 mmol) was added in portions during 15 minutes and afterwards 8-[(4-bromophenyl)methyl]-5,8-dihydro-2,4 -dimethyl-pyrido[2,3-d]pyrimidin-7(6H)-one (4.15 g; 12 mmol), palladium acetate (0.04 g; 0.18 mmol) and triphenylphosphine (0.142 g; 0.54 mmol) were added. The mixture was kept under stirring at 60° C. for 24 hours.

The mixture, analysed by HPLC analysis, contains:

coupling product: 2.99 g (7.3 mmol)

starting material: 1.5 g (4.6 mmol)

EXAMPLE 3

Ethylbromide (2.2 g; 20 mmol) was added dropwise to a stirred suspension of magnesium (0.488 g; 20 mmol) in tetrahydrofuran (10 ml), at 25° C. under inert atmosphere, keeping the temperature below 60° C. The mixture was kept under stirring for 30 minutes; then diisopropylamine (0.4 g, 4 mmol) was added and it was refluxed (73° C.) for 1 hour. Phenyl-tert-butyltetrazole (3.2 g; 16 mmol) was added and it was refluxed (73° C.) for 28 hours.

The $^1H$-NMR analysis pointed out the presence of about 80% of ortho-metalled product.

EXAMPLE 4

2,2,6,6-Tetramethylpiperidine (1.33 g; 9.43 mmol) was added to a 23% mixture of methylmagnesium chloride in THF (69.1 g; 213 mmol), warmed at reflux and under stirring. The mixture was kept under stirring for 10 minutes, then phenyl-tert-butyltetrazole (38.1 g; 188 mmol) was added and it was refluxed, under stirring, for 45 hours.

The $^1H$-NMR analysis of a sample pointed out the presence of about 88% of ortho-metalled product. The mixture was cooled at 40° C., then tetrahydrofuran (48 ml), toluene (157 ml) and anhydrous zinc chloride (51 g; 375 mmol) were added. keeping the temperature under 60° C. The resultant suspension was kept under stirring at 60° C. for 2 hours. 8-[(4-Bromophenyl)methyl]-5,8-dihydro-2,4-dimethyl-pyrido[2,3 -d]pyrimidin-7(6H)-one (45 g; 130 mmol), palladium acetate (0.44 g; 1.95 mmol) and triphenylphosphine (1.5 g; 5.8 mmol) were added and the mixture was kept at 60° C. for 4 hours. The suspension was cooled at 25° C., water (90 ml) and acetic acid (15 ml) were added.

The two phases were separated and the organic one was evaporated to dryness under vacuum.

The residue, analysed by HPLC analysis, contains:

coupling product: 55.6 g (119 mmol; y=91%)

starting material: <0.5%

EXAMPLE 5

2,2,6,6-Tetramethylpiperidine (0.31 g; 2.21 mmol) was added to a 2 M mixture of benzylmagnesium chloride in THF (24.4 ml, 49 mmol), warmed at reflux and under stirring. The mixture was kept under stirring for 10 minutes, then phenyl-tert-butyltetrazole (8.95 g; 44 mmol) was added and it was refluxed, under stirring, for 45 hours.

The $^1$H-NMR analysis of a sample pointed out the presence of about 80% of ortho-metalled product.

EXAMPLE 6

Ethylbromide (6.3 g; 58 mmol) was added dropwise to a stirred suspension of magnesium turnings (1.27 g; 52.5 mmol) in tetrahydrofuran (10 ml), at 25° C. under inert atmosphere, keeping the temperature below 60° C., At the end of the addition, the mixture was stirred at reflux temperature; then 2,2,6,6-tetramethylpiperidine (0.31 g; 2.21 mmol) was added and it was refluxed for 10 minutes. Phenyl-tert-butyltetrazole (8.95 g; 44 mmol) was added and the mixture was kept under stirring, at reflux, for 25 hours. The $^1$H-NMR analysis of a sample pointed out the presence of about 79% of ortho-metalled product.

EXAMPLE 7

Ethylbromide (39.2 g; 360 mmol) was added dropwise to a stirred suspension of magnesium turnings (9.1 g; 374 mmol) in tetrahydrofuran (180 ml), at 25° C. under inert atmosphere, keeping the temperature below 60° C. At the end of the addition, the mixture was refluxed for 30 minutes under stirring, then 2.2,6,6-tetramethylpiperidine (2.23 g; 16 mmol) was added and it was refluxed for further 10 minutes. Phenyl-tert-butyltetrazole (129 g; 639 mmol) was added and the mixture was kept under stirring, at reflux, for 19 hours. It was then cooled at 40° C., toluene (330 ml) and anhydrous zinc chloride (81 g; 593 mmol) were added. keeping the temperature below 60° C. The suspension was kept under stirring at 60° C. for 2 hours, then 8-[(4-bromophenyl)methyl]-5,8-dihydro-2,4-dimethyl-pyrido[2,3-d]pyrimidin-7(6H)-one (81 g; 234 mmol), palladium acetate (0.79 g; 3.5 mmol) and triphenylphosphine (2.8 g; 10.6 mmol) were added. The mixture was kept under stirring at 60° C. for 18 hours. The suspension was cooled at 25° C., then water (120 ml) and acetic acid (15 ml) were added. The phases were separated and the organic phase was evaporated under vacuum.

The residue, analysed by HPLC analysis, contains:
coupling product: 87.5 g (187 mmol, y=80%)
starting material: lower then 0.5%

COMPARISON EXAMPLE 1

Ethylbromide (2.2 g; 20 mmol) was added dropwise to a stirred suspension of magnesium turnings (0.48 g; 20 mmol) in tetrahydrofuran (10 ml), at 25° C. under inert atmosphere, keeping the temperature below 60° C. The mixture was kept under stirring for 30 minutes; phenyl-tert-butyltetrazole (4.0g; 20 mmol) was added and it was refluxed (73° C.) for 3 hours. There was no evolution of gas and the $^1$H-NMR analysis did not detect any ortho-metalled product.

COMPARISION EXAMPLE 2

Ethylbromide (4.4 g; 40 mmol) was added dropwise to a stirred suspension of magnesium (0.96 g; 40 mmol) in tetrahydrofuran (20 ml), at 25° C. under inert atmosphere, keeping the temperature below 60° C. At the end of the addition, the mixture was stirred for 30 minutes; then 2,2,6,6-tetramethylpiperidine (5.8 g; 40 mmol) was added and it was refluxed (73° C.) for 2 hour until the evolution of gas stopped. Phenyl-tert-butyltetrazole (1.35 g; 6.6 mmol) was added and it was refluxed (73° C.).

The course of the ortho-metalation reaction was evaluated by $^1$H-NNR analysis, with the following results:
after 1.5 hours 56% of metalled product
after 3.0 hours 60% of metalled product
after 4.0 hours 58% of metalled product.

What is claimed is:

1. A process of direct ortho-metalation for the preparation of compounds of formula

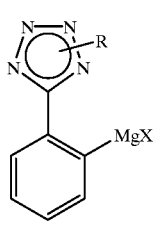

(II)

in which
R is a hydrogen atom, a protective group or a salifying group and X is a halogen atom selected among chlorine, bromine or iodine;
which comprises the treatment of a compound of formula

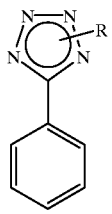

(III)

in which R has the above reported meanings; with a Grignard compound of formula $R_1MgX$ (IV)

in which X has the just reported meanings and $R_1$ is a straight or branched $C_1$–$C_6$ alkyl group or a benzyl group; in the presence of a catalytic amount of a secondary amine of formula $R_2$-NH-$R_3$ (V)

in which $R_2$ and $R_3$, the same or different, are branched or cyclic $C_3$–$C_6$ alkyl groups or trialkylsilyl groups having from 1 to 3 carbon atoms in the alkyl moiety or $R_2$ and $R_3$ together with the NH group form an optionally substituted cyclic amine.

2. A process according to claim 1 in which the molar ratio compound IV: compound III is between 1:1 and 1.5:1.

3. A process according to claim 2 in which the molar ratio is between 1.05:1 and 1.3:1.

4. A process according to claims 1, 2 or 3 in which compound IV is an ethylmagnesium halide.

5. A process according to claim 4 in which compound IV is ethylmagnesium bromide.

6. A process according to claim 1 in which the molar ratio compound V: compound IV is between 0.01:1 and 0.5:1.

7. A process according to claim 6 in which the molar ratio is between 0.05:1 and 0.2:1.

8. A process according to claim 1 in which the compound V is selected among diisopropylamine, di-tert-butylamine, di-sec-butylamine, tert-butyl-iso-propylamine, di-cyclopentylamine, di-cyciohexylaamine, 2,2,6,6-tetramethylpiperidine and 2,2,5,5,-tetramethylpyrrolidine.

9. A process according to claim 8 in which the compound V is selected between dilsopropylamine and 2,2,6,6-tetramethylpiperidine.

10. A process for the preparation of compounds of formula I

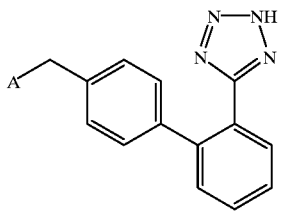

(I)

wherein A is an optionally substituted nitrogen containing heterocycle or an open amide residue that comprises a process of direct ortho-metalation according to claim 1.

11. A process according to claim 10 for the preparation of tasosartan.

* * * * *